(12) United States Patent
Nakazawa et al.

(10) Patent No.: US 7,573,030 B2
(45) Date of Patent: Aug. 11, 2009

(54) SPECIMEN OBSERVATION METHOD

(75) Inventors: Eiko Nakazawa, Mito (JP); Masahiro Tomita, Hitachinaka (JP); Hiroyuki Kobayashi, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 309 days.

(21) Appl. No.: 11/717,155

(22) Filed: Mar. 13, 2007

(65) Prior Publication Data

US 2008/0073527 A1 Mar. 27, 2008

(30) Foreign Application Priority Data

Mar. 14, 2006 (JP) ............................. 2006-068472

(51) Int. Cl.
*G21K 7/00* (2006.01)
(52) U.S. Cl. .................. 250/307; 250/306; 250/310; 250/311; 250/397; 250/400
(58) Field of Classification Search ................ 250/306, 250/307, 310, 311, 397, 400
See application file for complete search history.

(56) References Cited

U.S. PATENT DOCUMENTS

| | | | |
|---|---|---|---|
| 5,646,403 A | | 7/1997 | Mori et al. |
| 6,838,667 B2 * | | 1/2005 | Tsuneta et al. ................. 850/10 |
| 2001/0002697 A1 * | | 6/2001 | Hiroi et al. .................... 250/310 |
| 2001/0033683 A1 * | | 10/2001 | Tanaka et al. ................ 382/149 |
| 2002/0088940 A1 * | | 7/2002 | Watanabe et al. ............ 250/310 |
| 2002/0181756 A1 * | | 12/2002 | Shibuya et al. ............... 382/145 |
| 2005/0168731 A1 * | | 8/2005 | Shibuya et al. ............ 356/237.4 |
| 2007/0176103 A1 * | | 8/2007 | Inada et al. ................... 250/311 |
| 2007/0284526 A1 * | | 12/2007 | Nara et al. .................... 250/307 |

FOREIGN PATENT DOCUMENTS

| | | |
|---|---|---|
| JP | 6-13011 A | 1/1994 |
| JP | 8-129986 A | 5/1996 |

* cited by examiner

*Primary Examiner*—David A Vanore
*Assistant Examiner*—Michael J Logie
(74) *Attorney, Agent, or Firm*—McDermott Will & Emery LLP

(57) ABSTRACT

It is an object of the present invention to provide a specimen observation method, an image processing device, and a charged-particle beam device which are preferable for selecting, based on an image acquired by an optical microscope, an image area that should be acquired in a charged-particle beam device the representative of which is an electron microscope. In the present invention, in order to accomplish the above-described object, there are provided a method and a device for determining the position for detection of charged particles by making the comparison between a stained optical microscope image and an elemental mapping image formed based on X-rays detected by irradiation with the charged-particle beam.

3 Claims, 3 Drawing Sheets

SPECIMEN OBSERVATION METHOD

BACKGROUND OF THE INVENTION

1. Field of the Invention

The present invention relates to a specimen observation method, an image processing device, and a charged-particle beam device. More particularly, it relates to a method and a device which are preferable for observing the same field-of-view as that of a specimen observed using an optical microscope.

2. Description of the Related Art

Concerning a specimen to be observed using an optical microscope, in the case of, e.g., a living-creature specimen, the specimen can be colored by an appropriate staining method which depends on differences in the specimen components and its physiological state. As a result, the specimen can be observed in a state which is close to that of a living body. By the way, in the analysis of living-body reactions like this, fine structure analysis at cell level or macromolecular level is important. An optical microscope, however, finds it difficult to observe the fine structure. This is because the optical microscope has a limitation to its resolving power, and thus can exhibit only an insufficient magnification. Accordingly, for this fine structure analysis to be implemented, the observation made by an electron microscope is desirable.

In JP-A-6-13011, the following explanation has been given: A specimen is observed using an optical image capture device provided independently of an electron microscope. Moreover, its coordinate position and the position of specimen stage of the electron microscope are made to correspond to each other, thereby searching for field-of-view in the electron microscope.

In JP-A-8-129986 (corresponding to U.S. Pat. No. 5,646,403), the following explanation has been given: Regarding field-of-view displacement of a scanning electron microscope, the specimen stage is displaced in correspondence with observation field-of-view width of the scanning electron microscope.

An optical microscope performs formation of a specimen image mainly by detecting reflection light from the specimen. In contrast thereto, however, an electron microscope performs formation of a specimen image by detecting secondary electrons and the like. In this way, since the specimen images are formed based on the different signals, the image qualities are exceedingly different from each other. Consequently, it has been difficult to retrieve the observation field-of-view of the electron microscope on the basis of the specimen image acquired using the optical microscope.

SUMMARY OF THE INVENTION

It is an object of the present invention to provide a specimen observation method, an image processing device, and a charged-particle beam device which are preferable for selecting, based on an image acquired by an optical microscope, an image area that should be acquired in a charged-particle beam device the representative of which is an electron microscope.

In the present invention, in order to accomplish the above-described object, there are provided a method and a device for determining the position for detection of charged particles by making the comparison between a stained optical microscope image and an elemental mapping image formed based on X-rays detected by irradiation with the charged-particle beam. The configuration like this makes it possible to easily implement that, e.g., a reaction region within an optical microscope image to which a staining corresponding to a living-body reaction has been applied is set and employed as the observation target of a charged-particle beam device such as an electron microscope.

According to the present invention, it becomes possible to easily implement a search for field-of-view for the observation by a charged-particle beam device with respect to a specimen observed using an optical microscope.

Other objects, features and advantages of the invention will become apparent from the following description of the embodiments of the invention taken in conjunction with the accompanying drawings.

DESCRIPTION OF THE INVENTION

Figure 1:
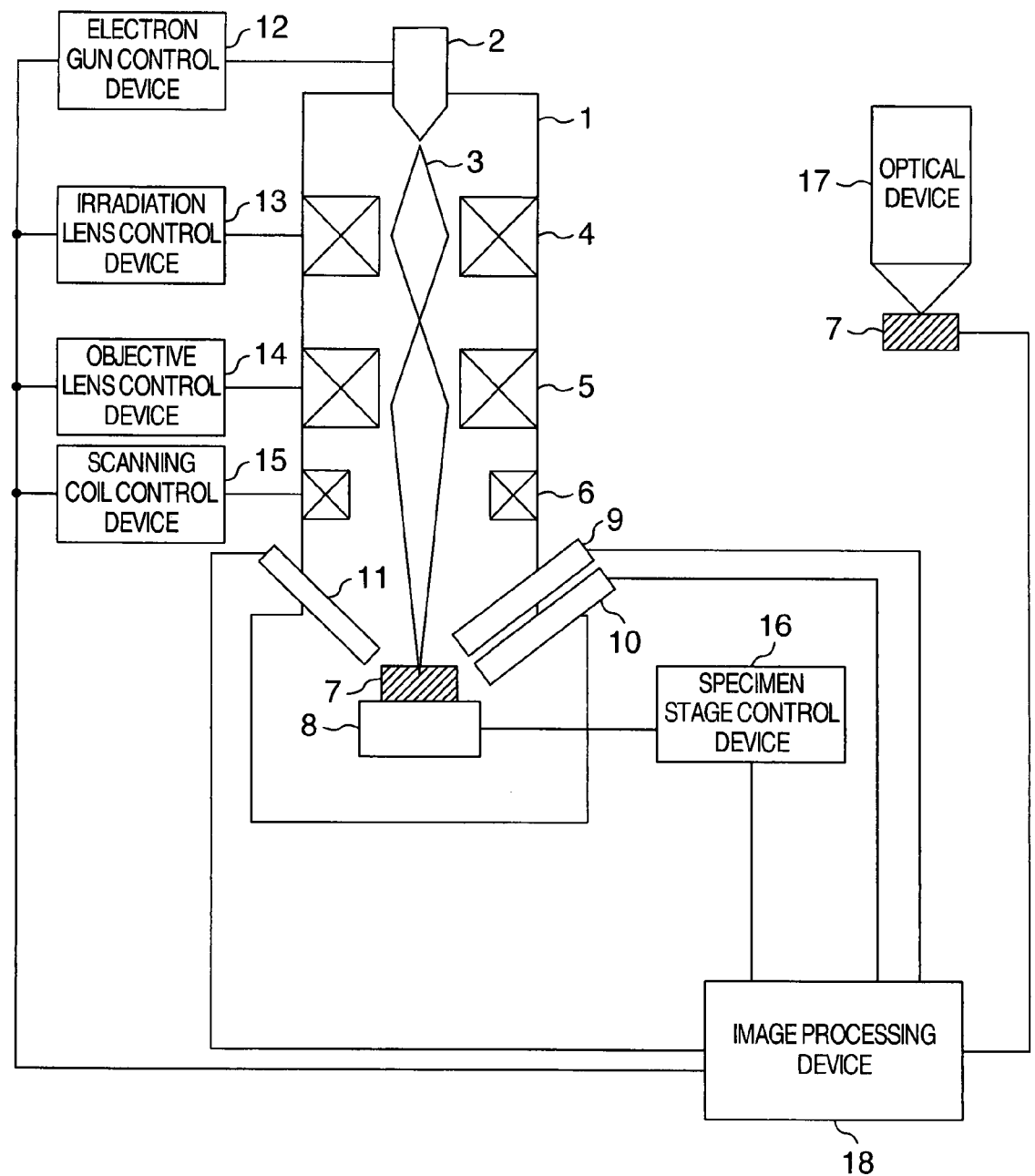
FIG. 1 is a diagram for explaining an example of a scanning electron microscope.

Hereinafter, referring to the drawings, the detailed explanation will be given below concerning an example of a charged-particle beam device in order to explain an embodiment of the present invention.

Embodiment 1

As a charged-particle beam device, there exists a scanning electron microscope, transmission electron microscope, scanning transmission electron microscope, or ion beam irradiation device. In the present example, the explanation will be given below regarding an embodiment of the present invention, referring to FIG. 1 and selecting a scanning electron microscope as the example.

As illustrated in the drawing, an electron beam 3 emitted from an electron gun 2 of main body of an electron microscope 1 is converged by an irradiation lens 4. Next, the electron beam 3 is deflected by a scanning coil 6 including an X-direction deflection coil and a Y-direction deflection coil. Moreover, the electron beam 3 deflected into the two directions is focused on a specimen 7 held by a specimen stage 8 by an objective lens 5, then being scanned on the specimen 7.

The electron gun 2 is controlled by an electron gun control device 12. The irradiation lens 4 and the objective lens 5 are controlled by an irradiation lens control device 13 and an objective lens control device 14, respectively. Also, a not-illustrated specimen stage driving mechanism is controlled by a specimen stage control device 16. The scanning coil 6 is controlled by a scanning coil control device 15.

These devices, i.e., the electron gun control device 12, the irradiation lens control device 13, the objective lens control device 14, the scanning coil control device 15, and the specimen stage control device 16, configure an observation condition setting device.

Characteristic X-rays are generated from surface of the specimen 7 by the electron beam 3 scanned on the specimen 7. Next, the characteristic X-rays generated are detected by an X-ray detector 11, and are supplied to an image processing device 18, then being recorded and stored as image data. Simultaneously, secondary electrons generated from the specimen 7 are detected by a secondary-electron detector 9, and are supplied to the image processing device 18 as image data, then being recorded and stored. Simultaneously, reflection electrons generated from the specimen 7 are detected by a reflection-electron detector 10, and are supplied to the image processing device 18 as image data, then being recorded and stored.

An optical image, which is acquired by an optical device 17 independently of the electron microscope, is supplied to the image processing device 18, then being recorded and stored as image data.

In this embodiment, the observation condition setting device of the electron microscope, i.e., each of the electron gun control device 12, the irradiation lens control device 13, the objective lens control device 14, the scanning coil control device 15, and the specimen stage control device 16, is so configured as to be connected to the image processing device 18 via a predetermined transmission path so that the mutual data transmission/reception is executable. Also, the image processing device 18 is so configured as to allow implementation of the driving control over the specimen stage and setting of the observation conditions for each lens.

On account of this, the image processing device 18 is so configured as to include, e.g., a computer onto which a predetermined program is installed. This program makes it possible to create control data which is necessary for the above-described specimen-stage driving mechanism control device and observation condition setting device, and which should be supplied thereto.

Figure 2:
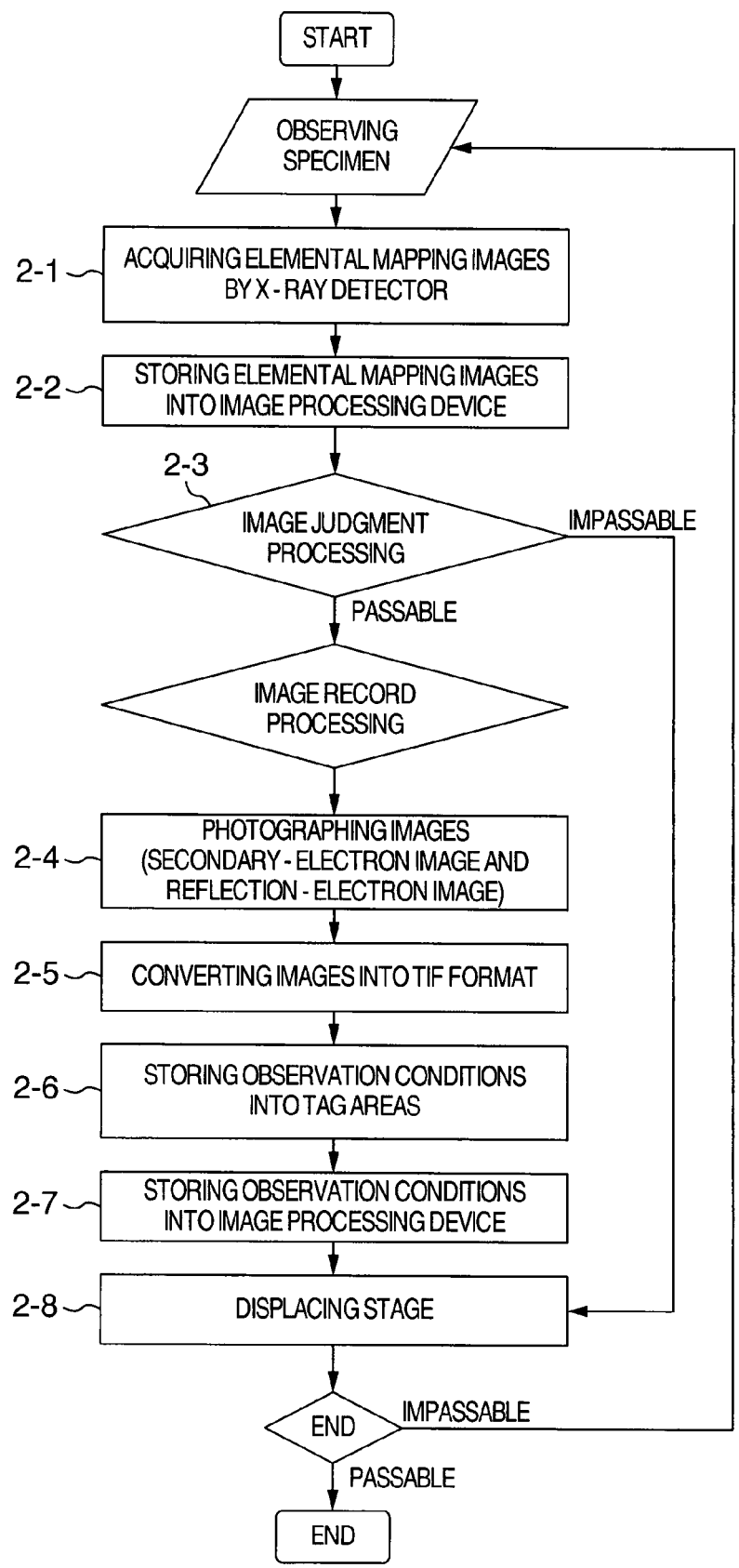
FIG. 2 is a flowchart (the first part) for illustrating operation of an embodiment of the present invention.

Hereinafter, referring to a flowchart in FIG. 2, the explanation will be given below concerning an example of the operation when the same field-of-view as that of a specimen image captured using an optical device is observed using a charged-particle beam device.

In the present embodiment, "image judgment processing", "image record processing", "image retrieval processing", and "condition registration processing" are carried out by the image processing device 18.

First, using the optical microscope, the operator observes the specimen 7 which is stained for the optical microscope. Although not illustrated in FIG. 1, the specimen image observed is photographed by a record device such as CCD camera. After that, the photographed image is supplied to the image processing device 18.

Next, the specimen 7 for the optical microscope is set on the specimen stage 8 inside a specimen chamber of the scanning electron microscope. Moreover, the electron beam 3 is scanned on the surface of the specimen 7 in accordance with a predetermined procedure, and resultant characteristic X-rays generated are detected by the X-ray detector 11 (step: 2-1). In addition, elemental mapping images where intensity of the characteristic X-rays detected by the X-ray detector 11 is displayed in a two-dimensional manner is supplied to the image processing device 18, then being recorded and stored as image data (step: 2-2).

Subsequently, in the image processing device 18, the comparison is made between the image data on the specimen image by the optical microscope and the elemental mapping images. At this time, it is advisable to use an image correlation method. Result of the image correlation, which is the degree of coincidence between both of the images, may be displayed as "coincidence degree".

If an elemental mapping image exhibiting the highest coincidence degree has been successfully selected out of the result by the image correlation (step: 2-3), a secondary-electron image and a reflection-electron image within the field-of-view are observed (step: 2-4). Incidentally, in the present embodiment, a predetermined threshold value may be set in advance regarding the coincidence degree of the images, and an image which is found to exceed this threshold value may be selectively acquired, observed, and recorded.

Simultaneously with the acquisition of the elemental mapping image of the specimen image acquired by the image optical device, the secondary-electron image and the reflection-electron image within the field-of-view may be observed, and be recorded into the image processing device 18 as the image data. These series of image data, i.e., the specimen image acquired by the optical device, its elemental mapping image, and its secondary-electron image and reflection-electron image, may be recorded into the image processing device 18 as a single data group.

At this time, the observation conditions of the optical microscope have been supplied to the observation condition setting device of the electron microscope via the image processing device 18. As a result, the observation conditions in the electron microscope coincide with the observation conditions of the optical microscope. In the image data groups, in the case of the image data stored in, e.g., TIF image format (step: 2-5), all the observation conditions of the observation condition setting device of the electron microscope may be written into tag areas, thereby being recorded in a manner of being made to correspond to the images (step: 2-6, step: 2-7). Moreover, the specimen stage is displaced to the next observation position (step: 2-8), then returning to observation of the specimen depending on the requirements. Hereinafter, basically the same steps will be executed.

Figure 3:
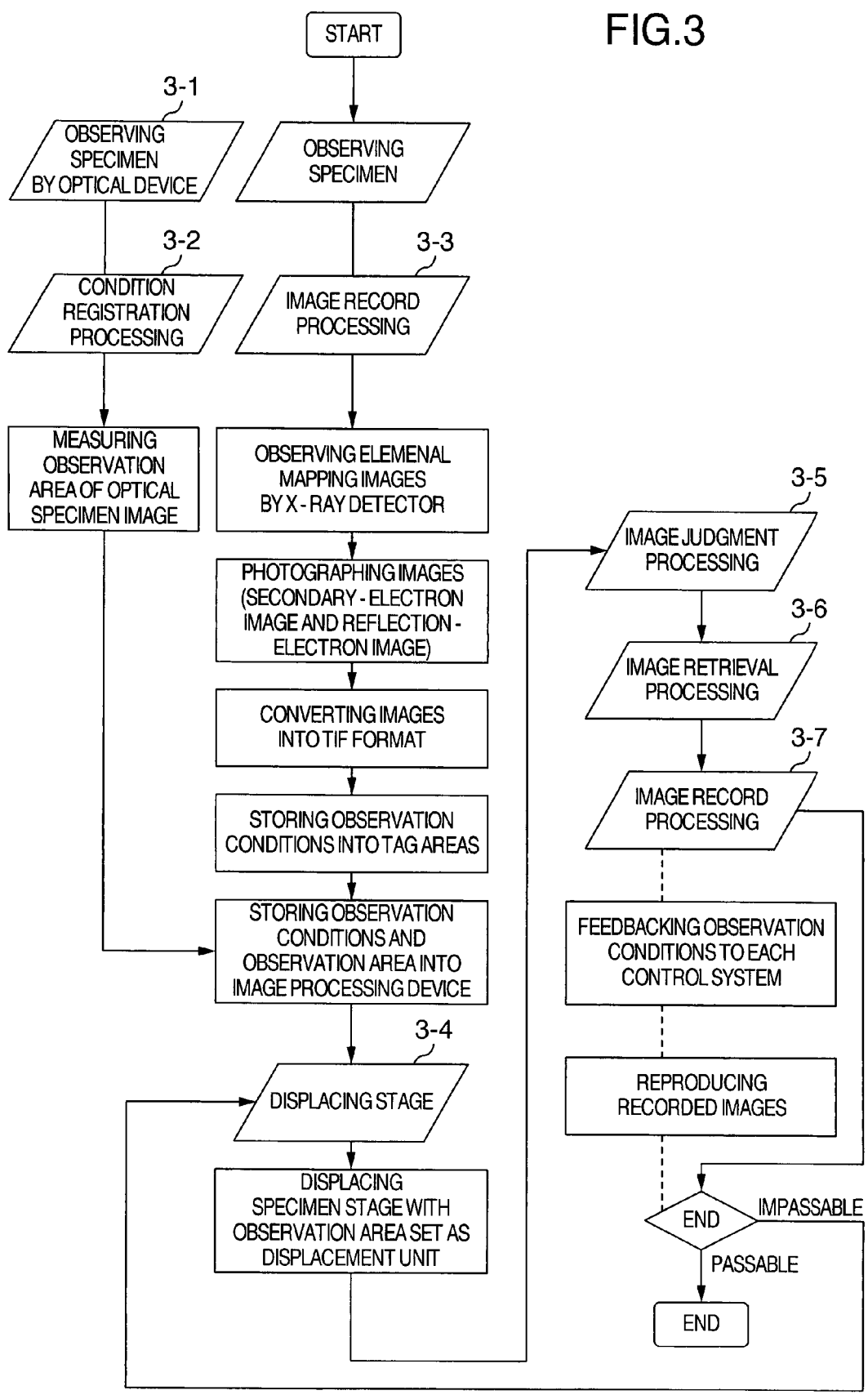
FIG. 3 is a flowchart (the second part) for illustrating the operation of the embodiment of the present invention.

Next, in this embodiment, the same field-of-view is automatically searched for by performing displacement of the specimen stage in such a manner that the observation area by the optical device is selected and defined as the unit of this displacement. Referring to a flowchart in FIG. 3, the explanation will be given below concerning the operation at this time.

With respect to the specimen image by the optical microscope, the observation field-of-view area of the optical microscope is determined from the image data supplied to the image processing device 18 (step: 3-1). The specimen stage 8 is controlled by the specimen stage control device 16 of the electron microscope in such a manner that the specimen stage 8 displaces with the observation field-of-view area as the unit of the displacement amount of the specimen stage (step: 3-2).

Acquisition positions of the elemental mapping of the optical microscope specimen by the X-ray detector 11 are read by the specimen stage control device 16, then being recorded in a manner of being made to correspond to the elemental mapping images (step: 3-3). The results of the image correlation between the elemental mapping of the optical microscope specimen by the X-ray detector 11 and the optical microscope specimen images are displayed as, e.g., the coincidence degrees (step: 3-4).

Depending on rank of the coincidence degrees by the image correlation between the elemental mapping of the optical microscope specimen by the X-ray detector 11 and the optical microscope specimen images, the elemental mapping images, secondary-electron images, and reflection-electron images of the specimen are ranked. The optical microscope specimen images, the elemental mapping images of the optical microscope specimen by the X-ray detector, the secondary-electron images, and the reflection-electron images are recorded and stored into the image processing device 18 as the data group (step: 3-5). Also, in this embodiment, the specimen stage control device 16 may be controlled so that the specimen stage 8 displaces in such a manner that the acquisition area of the elemental mapping of the optical microscope specimen by the X-ray detector 11 is selected and defined as the displacement amount of the specimen stage. As the result of the image correlation between the elemental mapping images of the optical microscope specimen by the X-ray detector 11 and the optical microscope specimen images, if the highest coincidence degree is found, or if a coincidence degree is found to exceed a predetermined threshold value, the displacement of the specimen stage 8 is halted. Then, its position coordinate at this time is recorded and stored (step: 3-6).

Consequently, according to this embodiment, it becomes possible to directly observe the specimen for the optical microscope in the scanning electron microscope without preparing a specific specimen manufacturing intended for the scanning electron microscope. On account of the image correlation between the elemental mapping images of the specimen for the optical microscope and the specimen images acquired by the optical device, the same field-of-view as that of the observation region of the specimen for the optical microscope can be observed by the scanning electron microscope. The reaction region of the specimen for the optical microscope to which a staining corresponding to a living-body reaction has been applied can be directly observed by the electron microscope. This makes it possible to directly observe the relationship between the living-body reaction and the fine structure. Moreover, the specimen stage is displaced in such a manner that the acquisition area of the elemental mapping images of the optical microscope specimen is selected and defined as the unit of the displacement amount. Then, these pieces of coordinate information are stored in a manner of being made to correspond to the elemental mapping images. Furthermore, the elemental mapping images of the optical microscope specimen, the secondary-electron images, and the reflection-electron images are stored as the data group, then being ranked depending on the coincidence degrees. Then, the displacement of the specimen stage can be automatically halted at the position at which the highest coincidence degree is found.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A specimen observation method whereby locations on a specimen displayed on an optical microscope image acquired by an optical microscope are observed by a charged-particle beam device, said specimen observation method, comprising the steps of:
    staining said optical microscope image for being acquired by said optical microscope,
    acquiring said optical microscope image by said optical microscope,
    acquiring an elemental mapping image based on detection of X-rays, said X-rays being emitted from said specimen when said specimen is scanned with said charged-particle beam,
    making a comparison between said optical microscope image stained and said elemental mapping image, and
    scanning locations on said specimen or a location on said specimen with said charged-particle beam, coincidence degrees between said optical microscope image stained and said elemental mapping image exceeding a predetermined value at said locations on said specimen, said coincidence degree being the highest at said location on said specimen, and
    detecting said charged particles, and/or detecting position information on said locations or said location.

2. The specimen observation method according to claim 1, wherein
    said locations on said specimen are ranked in a descending order of said coincidence degrees.

3. The specimen observation method according to claim 1, wherein
    a charged-particle beam image at said locations on said specimen and/or said location on said specimen, or said position information on said locations and/or said location are recorded as a single file, said coincidence degrees between said optical microscope image and said elemental mapping image exceeding said predetermined value at said locations on said specimen, said coincidence degree being the highest at said location on said specimen.

* * * * *